United States Patent [19]

Herlihy et al.

[11] Patent Number: 4,476,300

[45] Date of Patent: Oct. 9, 1984

[54] N-OXIDE OF THE O-β-D GLUCURONIDES OF ANTICHOLINERGIC COMPOUNDS, AND PROCESS FOR PREPARING THE SAME

[75] Inventors: Walter C. Herlihy, Cambridge; David M. Epstein, Belmont, both of Mass.

[73] Assignee: Repligen Corporation, Cambridge, Mass.

[21] Appl. No.: 520,497

[22] Filed: Aug. 4, 1983

[51] Int. Cl.³ .......................................... C07H 15/18
[52] U.S. Cl. .................. 536/17.4; 536/18.1; 536/18.2; 536/17.7; 546/268
[58] Field of Search .............. 546/268; 536/17.4, 18.1, 536/18.2, 7.4, 17.7

[56] References Cited

U.S. PATENT DOCUMENTS

| | | | |
|---|---|---|---|
| 3,240,777 | 3/1966 | Sarett et al. | 260/239.55 |
| 3,624,200 | 11/1971 | Moffett | 424/65 |
| 3,767,786 | 10/1973 | MacMillan | 424/65 |
| 3,928,387 | 12/1975 | Kierstead et al. | 536/7.4 |
| 4,153,697 | 5/1979 | Hornke et al. | 424/258 |
| 4,292,250 | 9/1981 | DeLuca et al. | 260/397.2 |

OTHER PUBLICATIONS

Salam and Isbell, Reactions of Methyl Aldohexopyranosides with Alkaline Hydrogen Peroxide, Carbohydro. Res. 101, 255 (1982).

Weaver et al., Formation of Organic Peroxides from Methyl β-D-Glucopyranoside in Alkaline Hydrogen Peroxide Solutions, Carbohydr. Res. 48, C5 (1976).

Yamane, et al., Biochemical Studies on Glucuronides, Yakugaku Zasshi 87(3), 227 (1967) (Japan), Chem. Abstracts, vol. 67, p. 1123 (1967)–Abstract No. 11688q.

*Primary Examiner*—Johnnie R. Brown
*Attorney, Agent, or Firm*—Roman Saliwanchik

[57] ABSTRACT

The subject invention concerns a novel process for preparing novel N-oxide compounds of O-β-D-glucuronides of an anticholinergic compound containing a tertiary nitrogen. Examples of suitable glucuronide starting materials are O-β-D-glucuronides of tropicamide, scopolamine, atropine, hyoscyamine, and the like. The novel process gives high yields of the desired N-oxides which are useful as UV filters.

11 Claims, No Drawings

N-OXIDE OF THE O-β-D GLUCURONIDES OF ANTICHOLINERGIC COMPOUNDS, AND PROCESS FOR PREPARING THE SAME

DESCRIPTION

BACKGROUND OF THE INVENTION

The synthesis of the glucuronides of ester-containing compounds is difficult to carry out by conventional synthetic chemical techniques such as the Koenigs-Knorr reaction. The difficulty of such techniques makes them impractical for the preparation of essentially pure preparations of desired glucuronides. In order to overcome this problem, enzymatic processes were invented to prepare desired glucuronide compounds.

In one such enzymatic process the O-β-D-glucuronide of scopolamine, an ester-containing alkaloid, was prepared by the use of UDPGA transferase (EC 2.4.1.17) in the presence of an esterase inhibitor. In another process the O-β-D-glucuronide of scopolamine was synthesized by the β-glucuronidase (EC 3.2.1.31)-catalyzed reaction of scopolamine and glucuronic acid. These processes are disclosed herein.

Attempts to prepare the N-oxide of the O-β-D-glucuronide of scopolamine by use of scopolamine N-oxide as the starting material in the above enzymatic processes resulted in the obtention of low yield of desired product. This low yield made it impossible to isolate sufficient quantities of desired product.

Thus, methods reasonably suggested by the prior art do not afford sufficient quantities of the N-oxide of the O-β-D-glucuronide of scopolamine which can be isolated, much less essentially pure preparations of this product.

Though the O-β-D-glucuronide of scopolamine is specifically disclosed herein, it is merely exemplary of the scope of glucuronide compounds which can be used to make novel N-oxides. Generically, the scope of glucuronide starting material encompasses the O-β-D-glucuronides of an anticholinergic compound which contains a tertiary nitrogen. Examples of such compounds, in addition to the O-β-D-glucuronides of scopolamine, are the O-β-D-glucuronides of tropicamide, atropine, hyoscyamine, and the like.

The subject process for the preparation of the N-oxides of the O-β-D-glucuronide of an anticholinergic compound which contains a tertiary nitrogen gives the desired compounds in their essentially pure form. This is possible because the subject process, unexpectedly, gives sufficient yield of desired product; a yield which is considerably higher than that obtainable by what the prior art might reasonably suggest as a process for making such N-oxide products. We are not aware of any prior art process which has been used specifically to make the compounds of the subject invention.

BRIEF SUMMARY OF THE INVENTION

Novel N-oxides of the O-β-D-glucuronide of an anticholinergic compound which contains a tertiary nitrogen are prepared by treating said glucuronide with $H_2O_2$ in the presence of a chelating agent. Surprisingly, this chemical transformation gives a high yield of the desired product since it is well known that alkaline $H_2O_2$ will oxidize carbohydrates (see Salam, M. and Isbell, H. S. [1982] Carbohydr. Res. 101, 255; Weaver, J. W., Schroeder, L. R., and Thompson, N. S. [1976] Carbohydr. Res. 48, C5) and, thus, would be expected to degrade the glucuronic acid moiety. It has also been reported that $H_2O_2$ disassociates O-glucuronides. See Yamane, Y., Sakai, K., and Ikeguchi, K. (1967) Yakaguku Zasshi 87(3) 227. The success of the subject process in view of the prior art is clearly unexpected and advantageous.

The use of a chelating agent enhances significantly the yield of desired product. In the absence of the chelating agent a larger number of by-products are formed which reduce the yield to 10 to 20% and make isolation of pure desired product extremely difficult. Elimination of these side reactions with a chelating agent indicates the side-product formation is mediated by trace levels of metals which are present even in deionized water.

DETAILED DESCRIPTION OF THE INVENTION

The O-β-D-glucuronides of anticholinergics containing a tertiary nitrogen can be prepared, advantageously, by enzymatic processes. Examples of such processes are disclosed, infra.

In the subject invention process, the conversion of the glucuronide to the desired N-oxide compound is exemplified by use of the O-β-D-glucuronide of scopolamine. As stated previously, the O-β-D-glucuronide of an anticholinergic compound containing a tertiary nitrogen can be used as starting material to make novel and useful N-oxide products.

The conversion of the glucuronide starting material to the N-oxide can be carried out by dissolving the O-β-D-glucuronide (about 1 to about 50 mg/ml) in about 1 to about 30% $H_2O_2$ containing about 1 to about 50 mM of a chelating reagent and allowing the reaction to proceed for about 2 to about 48 hr at about 20° to about 65° C., advantageously, in subdued light or in the dark. Examples of chelating reagents which can be used are ethylenediaminetetraacetic acid (EDTA) and N,N-bis(carboxymethyl) glycine (nitrilotriacetic acid), and the like. The conversion can be carried out equally well at different concentration/time/temperature combinations, but the reaction must be monitored in order to achieve maximum yields (~90%).

The novel N-oxides of the subject invention are useful because of their absorption of ultraviolet light. These compounds can be used as ultraviolet absorbents in technical and industrial areas as follows:

(a) Textile materials; such textile materials may consist of natural materials of animal origin, such as wool or silk, or of vegetable origin, such as cellulosic materials of cotton, hemp, flax, or linen, and also semi-synthetic materials, such as regenerated cellulose, for example, artificial silk viscoses, including staple fibers of regenerated cellulose.

(b) Fibrous materials of other kinds (that is to say not textile materials) which may be of animal origin, such as feathers, hair, straw, wood, wood pulp or fibrous materials consisting of compacted fibers, such as paper, cardboard or compressed wood, and also materials made from the latter; and also paper masses, for example, hollander masses, used for making paper.

(c) Coating or dressing agent for textiles or paper.

(d) Lacquers or films of various compositions.

(e) Natural or synthetic resins.

(f) Filter layers for photographic purposes, especially for color photography.

Depending on the nature of the material to be treated, the requirements with regard to the degree of activity and durability, and other factors, the proportion of the light-screening agent to be incorporated in the material may vary within fairly wide limits, for example, from about 0.01% to 10%, and, advantageously, 0.1% to 2% of the weight of the material which is to be directly protected against the action of ultraviolet rays.

The following are illustrative of the invention, but are not to be construed as limiting. All percentages are by weight and all solvent mixture proportions are by volume unless otherwise noted.

PREPARATIONS OF ANTICHOLINERGIC GLUCURONIDE STARTING MATERIALS (a) Enzymatic preparation of (+,−) tropicamide O-β-D-glucuronide: Use of UDPGA transferase Four grams of a rabbit liver or bovine liver microsomal fraction (Sigma Chemical Co., St. Louis, Mo.) are suspended in 100 ml of a 75 mM tris hydrochloride buffer (pH=7.5-8.0). The microsomes are suspended by repeatedly drawing the mixture through a pipette tip. The microsomes are then pelleted by centrifugation at 100,000 g for 30 minutes. The supernatant is discarded, and the pellet is resuspended to 100 ml with a 150 mM tris hydrochloride (pH=7.5-8.0) solution, containing 200 mg (+,−) tropicamide (Hoffman-LaRoche, Nutley, N.J., also disclosed in U.S. Pat. No. 2,726,245) and 1 gram of sodium uridine 5'-diphosphoglucuronic acid (Sigma Chemical Co.). After a 20 hr incubation at 37° C., the reaction is terminated by heating to about 70° C., and centrifuging the reaction mixture. The desired product is in the supernatant. The yield of desired product is determined by high pressure liquid chromatography (HPLC) to be ~75%.

The HPLC conditions are as follows: A 0.39×30 cm C-18 μBondapak column (Waters Associates, Milford, Mass.) is eluted at 2 ml/min with 0.1% NH$_4$OAc (pH=5.75). After injection of the sample, a linear gradient to 60% methanol is applied to the column over a 20 min period. The column eluant is monitored with an ultraviolet detector set at 254 nm. Under these conditions the reaction product elutes as a partially resolved doublet. On the basis of chemical and spectral data the two peaks are assigned as (+) tropicamide O-β-D-glucuronide and (−) tropicamide O-β-D-glucuronide.

(b) Isolation of essentially pure (+),(−) tropicamide O-β-D-glucuronide

The pH of the reaction mixture, obtained in (a) is adjusted to 5.75 with 1.26 ml of 10% NH$_4$OAc (pH=5.75); 25 ml of methanol is added to the reaction, and the suspension is centrifuged at 44,000 g for 60 min. The supernatant is collected and loaded onto a 15 mm by 100 cm column of octadecyl derivatized silica (50-100μ particles) (Waters Associates) which had been equilibrated with an 80/20 solution of 0.1% NH$_4$OAc (pH=5.75)/methanol. The column is washed at 3 ml/min until the absorbency of the eluant at 254 nm is less than 0.05. Essentially pure (+),(−) tropicamide O-β-D-glucuronide is then eluted with a 55/45 solution of 0.1% NH$_4$OAc (pH=5.75)/methanol. Unreacted (+,−) tropicamide is eluted from the column with a 40/60 solution of 0.1% NH$_4$OAc (pH=5.75)/methanol. The desired product contains less than 1% of (+,−) tropicamide contamination.

(c) Separation of (+) and (−) tropicamide O-β-D-glucuronide

The two isomers are isolated from the mixture obtained in (b) as follows:

The two isomers are isolated by HPLC on a 0.39×30 cm column of C-18 μBondapak (Waters Associates). The column is equilibrated with 0.013 NH$_4$OAc (pH=3.7) containing 10% methanol at a flow rate of 2 ml/min. One minute after injection of the sample, the percentage of methanol in the eluant is raised to 22% in one minute. The two diastereomers elute at about 11 and 13 min respectively. Retention times vary with column condition and the optimal concentration of methanol is normally determined with analytical injections. The two diastereomers are obtained in their essentially pure form.

(d) Preparation of scopolamine O-β-D-glucuronic acid (SGA): Use of UDPGA transferase Four hundred milligrams of a rabbit liver or bovine liver microsomal fraction (Sigma Chemical Co.), containing uridine 5'-diphosphoglucuronyl transferase is suspended in 20 ml of a 75 mM tris HCl buffer (pH=8.0). The microsomes are suspended by repeatedly drawing the mixture through a pipette tip. The microsomes are then pelleted by centrifugation at 44,000 g for 20 min. The supernatant is discarded, the pellet washed a second time, and the pellet resuspended to 10 ml with a 75 mM tris HCl (pH=8.0) solution containing 20 mg scopolamine (Sigma) and 140 mg of sodium uridine 5'-diphosphoglucuronic acid (Sigma). In addition, the reaction mixture contains either 100 mM lysine ethyl ester (Sigma) or 10 μM phenylmethylsulfonyl fluoride (PMSF) (Sigma) which had been predissolved in a small volume of propanol immediately before addition. After a 20 hr incubation at 37° C., the reaction is terminated by heating the sample for 2 min at 70° C., followed by centrifugation at 44,000 g for 20 min. The supernatant is removed and analyzed by high pressure liquid chromatography (HPLC). The yield of desired product is determined to be ~95%.

The HPLC conditions are as follows: a 0.39×30 cm C-18 μBondapak column (Waters Associates) is eluted at 2 ml/min with 0.1% NH$_4$OAc (pH=7.5). After injection of the sample, a linear gradient to 60% methanol is applied to the column over a 20 min period. The column eluant is monitored with an ultraviolet detector set at 254 nm. Under these conditions the reaction product has a retention time of ~12 min, whereas scopolamine has a retention time of ~18 min. On the basis of chemical and spectral data the product is assigned as scopolamine O-β-D-glucuronide (SGA).

(e) Preparation of hyoscyamine O-β-D-glucuronic acid

The reaction conditions are identical to those utilized for scopolamine in (d). The concentration of hyoscyamine is 2 mg/ml and the reaction is carried out for 20 hr.

(f) Isolation of scopolamine O-β-D-glucuronide and hyoscyamine O-β-D-glucuronic acid The glucuronides are isolated by preparative reversed phase chromatography using a 100×1.5 cm column packed with Prep Bondapak C$_{18}$ (Waters Associates). The sample was loaded onto the column in 100 ml of 0.1% NH$_4$OAc (pH=7.5) and the column was washed at ~10 ml/min with two bed volumes of buffer, followed by two bed volumes of 12% CH$_3$OH in 0.1%

NH₄OAc (pH=7.5). The SGA was then eluted with 20% CH₃OH in 0.1% NH₄OAc (pH=7.5), concentrated by rotary evaporation and lyophilized.

Atropine O-β-D-glucuronic acid can be prepared by substituting atropine for hyoscyamine in the above-disclosed process.

The O-β-D-glucuronides of anticholinergics having a tertiary nitrogen can be prepared by following the procedures disclosed above for preparing scopolamine O-β-D-glucuronic acid.

(g) Synthesis of (+,−) tropicamide O-β-D-glucuronic acid: Use of β-glucuronidase A 1.7M sodium D-glucuronic acid stock solution is prepared by adding 16.5 gm of glucuronic acid to 40 ml of 50 mM sodium phosphate buffer; the pH is adjusted to ~6.8 with 5N NaOH, and the final volume is adjusted to 50 ml with 50 mM sodium phosphate (pH=6.8).

A 300 μl enzyme reaction is prepared by combining 100 μl of the 1.7M solution of sodium D-glucuronic acid, 100 μl of a 5 mg/ml solution of tropicamide, 30 μl of a 0.5M solution of sodium phosphate (pH=6.8), 50 μl of water and 20 μl of a 1000 Unit/ml solution of freshly dissolved E. Coli β-glucuronidase (EC 3.2.1.31) (Sigma Type VII, Sigma Chemical Co.). Immediately after addition of the enzyme, a 25 μl aliquot is removed and incubated at 70° C. for 1 min to inactivate the enzyme. A second aliquot is removed after a 20 hr incubation at 37° C. Both samples are diluted with an equal volume of 0.1% NH₄OAc (pH=5.75) and analyzed by high pressure liquid chromatography (HPLC) as follows: a 0.39×30 cm C-18 μBondapak column (Waters Associates) is eluted at 2 ml/min with 0.1% NH₄OAc (pH=5.75). After injection of the sample, a linear gradient to 60% methanol is applied to the column over a 20 min period. The column eluant is monitored with an ultraviolet detector set at 254 nm. Approximately 1% of the (+,−) tropicamide is converted to the corresponding O-β-D-glucuronic acid derivative.

(h) Separation of (+) and (−) tropicamide O-β-D-glucuronide

The two isomers are isolated from the mixture as described above in (c).

The ultraviolet spectra of (+),(−) tropicamide, (+) tropicamide O-β-D-glucuronide, and (−) tropicamide O-β-D-glucuronide are recorded in a 0.05% NH₄OAc (pH=7.0) solution. All three samples have identical spectra with maxima at 257 nm (Emax=2140) and shoulders at 252 nm and 263 nm characteristic of a para substituted pyridone moiety.

(i) Synthesis of scopolamine O-β-D-glucuronic acid: Use of β-glucuronidase

To a vial containing 1000 Units of lyophilized E. coli β-glucuronidase is added 300 μl of a 100 mg/ml solution of scopolamine, 2.4 ml of the 1.7M sodium glucuronic acid stock solution described above in (g), and 300 μl of a 0.5M sodium phosphate solution (pH=6.8). Samples (50 μl) are taken immediately after mixing and after a 20 hr incubation at 37° C. The enzyme is inactivated by heating as described above in (g). Scopolamine O-β-D-glucuronic acid exhibits UV maxima at 252 nm, 258 nm, and 263.5 nm, and a strong end absorption beginning at ~240 nm.

EXAMPLE 1

Preparation of scopolamine aminoxide O-β-D-glucuronic acid (SNOGA)

A solution of about 10 mg/ml of scopolamine O-β-D-glucuronic acid is dissolved in about 30% H₂O₂ containing about 10 mM EDTA. The reaction is allowed to proceed for about 7 hr at about 65° C., advantageously, in subdued light or in the dark to give SNOGA. It is well within the skill of a person in the art to vary the concentration of reactants, temperature, and time of reaction within the ranges specified previously to obtain the highest yield of N-oxide for the particular glucuronide used. As with most chemical reactions, longer reaction times will result in lower yields due to slower competing side reactions of the peroxide with the glucuronic acid moiety.

The SNOGA can be purified by the reversed phase liquid chromatography as described above in (f) for SGA with the following modification. After loading the sample the column is washed with one column volume of 0.1% NH₄OAc (pH=7.5) to remove the H₂O₂. The SNOGA is then eluted by washing the column with 1 to 2 column volumes of 7% CH₃OH, followed by 2 column volumes of 10% CH₃OH in 0.1% NH₄OAc (pH=7.5). Residual SGA is removed from the column by washing with a 50% solution of CH₃OH in NH₄OAc. Alternatively, in order to avoid the deleterious effects of H₂O₂ on the column, the H₂O₂ can be destroyed prior to the purification by a suitable reagent such as catalase.

Characterization of SNOGA

The ultraviolet spectrum of SNOGA was recorded in 0.05% NH₄OAc (pH=7) and showed three absorption maxima at 252 nm, 258 nm and 263 nm which are identical to the absorption maxima observed in the spectrum of scopolamine aminoxide.

Purified SNOGA (3.3 mg/ml) was treated with E. coli β-glucuronidase (1000 U/ml) for 60 min at 37° C. The SNOGA hydrolysis product chromatographed identically with a scopolamine aminoxide standard in two chromatographic systems. The first consisted of a 0.39×30 cm μBondapak C₁₈ column (Waters) eluted at 2 ml/min with 0.1% NH₄OAc (pH=7.5). After injection of ~20 μg of the sample, a linear gradient to 60% methanol was applied to the column in a 20 min period. The glucuronidase product and a scopolamine aminoxide standard both eluted at a retention time of 11.8 min. The second chromatographic system consisted of a 0.39×30 cm μBondapak Phenyl column eluted with a linear gradient from 0.1% NaOAc (pH=4.0), to 60% CH₃OH in 20 min. Both the hydrolysis product and the scopolamine N-oxide standard eluted at 11.5 min. The identical behavior of the hydrolysis product with the scopolamine aminoxide standard in two chromatographic systems proves that the product contains an intact scopolamine aminoxide moiety. The specificity of β-glucuronidase indicates that the product contains a β-glucuronide.

EXAMPLE 2

Upon substituting the O-β-D-glucuronide of an anticholinergic compound which contains a tertiary nitrogen for the O-β-D-glucuronide of scopolamine in Example 1, there is obtained the corresponding N-oxide of said glucuronide compound.

EXAMPLE 3

Salts with both inorganic and organic bases can be formed with the free acid of the compounds of the subject invention. For example, salts which can be formed are the ammonium, sodium, potassium, calcium, and the like, by neutralizing an aqueous solution of the free acid with the corresponding base. The base salts of the compounds of the subject invention are useful in the same manner as the free acid form.

Chart A discloses examples of the structures of O-β-D-glucuronides of anticholinergic compounds which contain a tertiary nitrogen. The N-oxides of these compounds can be made according to the process disclosed herein. Additionally, the N-oxide of the separate entities of (+),(−) tropicamide O-β-D-glucuronic acid, i.e., the (+) and (−) entities, can be made by the process disclosed herein.

CHART A
(+), (−) Tropicamide O—β-D-Glucuronic Acid

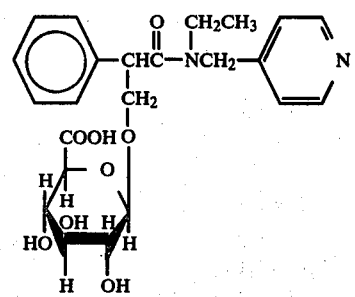

Scopolamine O—β-D-Glucuronic Acid

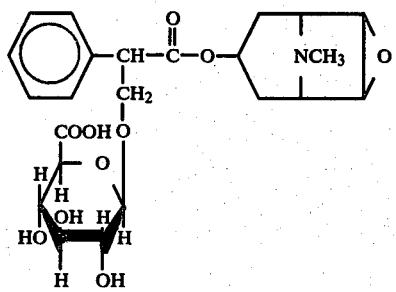

Hyoscyamine O—β-D-Glucuronic Acid

-continued
CHART A

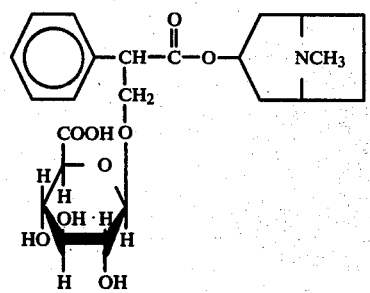

We claim:
1. The N-oxide of the O-β-D-glucuronide of an anticholinergic compound which contains a tertiary nitrogen, and base addition salts thereof.
2. Scopolamine aminoxide O-β-D-glucuronic acid, and base addition salts thereof.
3. The N-oxide of (+,−) tropicamide O-β-D-glucuronic acid, and base addition salts thereof.
4. The N-oxide of (+) tropicamide O-β-D-glucuronic acid, and base addition salts thereof.
5. The N-oxide of (−) tropicamide O-β-D-glucuronic acid, and base addition salts thereof.
6. The N-oxide of atropine O-β-D-glucuronic acid, and base addition salts thereof.
7. The N-oxide of hyoscyamine O-β-D-glucuronic acid, and base addition salts thereof.
8. A process for preparing the N-oxide of the O-β-D-glucuronide of an anticholinergic compound which contains a tertiary nitrogen, which comprises reacting said glucuronide at a concentration of about 1 to about 50 mg/ml with about 1 to about 30% $H_2O_2$ in the presence of about 1 to about 10 mM of a chelating agent for about 2 to about 48 hours at about 20° to about 65° C.
9. A process, according to claim 8, wherein said chelating agent is ethylenediaminetetraacetic acid or N,N-bis(carboxymethyl) glycine.
10. A process, according to claim 8, wherein said O-β-D-glucuronide is scopolamine O-β-D-glucuronic acid.
11. A process, according to claim 10, wherein a solution of about 10 mg/ml of scopolamine O-β-D-glucuronic acid is dissolved in about 30% $H_2O_2$ containing about 10 mM ethylenediaminetetraacetic acid and the reaction is allowed to proceed for about 7 hr at about 65° C. to give scopolamine aminoxide O-β-D-glucuronic acid.

* * * * *